United States Patent [19]
Baker et al.

[11] 3,981,980
[45] Sept. 21, 1976

[54] RADIOPHARMACEUTICALS FOR CHOLESCINTIGRAPHY

[75] Inventors: Richmond J. Baker, West Beach; Johan C. Bellen, Grange, both of Australia

[73] Assignees: The Council of the Institute of Medical and Veterinary Science; The University of Adelaide (Anti-Cancer Foundation), both of Adelaide, Australia

[22] Filed: Aug. 8, 1974

[21] Appl. No.: 495,875

[30] Foreign Application Priority Data
Aug. 24, 1973 Australia.............................. 4625/73

[52] U.S. Cl..................................... 424/1; 250/303; 260/429 R; 260/534 S
[51] Int. Cl.² ................. A61K 43/00; A61K 29/00; G01T 1/161; G21H 5/02
[58] Field of Search ......... 424/1; 260/429 R, 534 S; 250/303

[56] References Cited
OTHER PUBLICATIONS

McFarlane, "Biological Studies with Labelled Amino Acids and Proteins", Isotopes in Biochemistry and Physiology, Part 2, United Nations Publication, 1958.

*Primary Examiner*—Benjamin R. Padgett
*Assistant Examiner*—Christine M. Nucker
*Attorney, Agent, or Firm*—McNenny, Pearne, Gordon, Gail, Dickinson & Schiller

[57] ABSTRACT

A diagnostic substance for cholescintigraphy which is formed by the reaction of pyridoxal and amino acids labelled with a radionuclide, in pyrogen-free water, the reaction product being adjusted to a pH of 8 to 9 and then autoclaved and cooled to produce a sterile, pyrogen-free non-antigenic solution for injection for biliary scanning.

9 Claims, No Drawings

RADIOPHARMACEUTICALS FOR CHOLESCINTIGRAPHY

BACKGROUND OF INVENTION

At the present the only agent generally available for visualization of the gall bladder and biliary tract by scinti-scanning is $^{131}$I-rose bengal. This agent suffers many disadvantages among these being high radiation dose to the patient, poor resolution due to poor counting statistics and high gamma energy.

The use of technetium-99m in a gall bladder localizing radio-pharmaceutical will nullify most of these disadvantages. Reports describing two $^{99m}$Tc-compounds with this property have been published recently (in abstract form).

$^{99m}$Tc-D-penicillamine has been reported to accumulate in the gall bladder of dogs and is apparently excreted via the liver. It is stated that the gall bladder is well visualized 120–180 minutes after injection and that preliminary studies in man have been carried out, requiring 3 hours for good gall bladder accumulation. (Krishnamurthy, G.T., Tubis, M., Endow, J.S. and Blahd, W.H., $^{99m}$Tc-Penicillamine a new radio-pharmaceutical for cholescintigraphy. J. Nucl. Med. 13, 447 (1972). Further studies in humans have been reported more recently (Krishnamurthy, G.T., et al., $^{99m}$Tc-Penicillamine cholescintigraphy: comparison with oral cholecystography. J. Nucl. Med. 14, 418 (1973).

This time interval is undesirably long for an agent in routine use. Another disadvantage is the possibility of reactions in sensitive individuals, which have been described in cases where D-Penicillamine has been used therapeutically, (Crawhall, J.C., Further observations on use of D-penicillamine in cystinuria. Brit. Med. J. 1, 1411 1964).

A $^{99m}$Tc-labelled bile salt analogue has also been described. (Dugal, P., Eikman, E.A., Natarajan, T.K. and Wagner, H.N., Jr., A quantitative test of gall bladder function. J. Nucl. Med. 13, 428 (1972).

In dogs, this compound is said to accumulate rapidly within the liver and then move rapidly into the gall bladder. After a fatty meal, the gall bladder was observed to decrease in activity. In normal patients (Eikman, E.A., et al., Radioactive tracer techniques in the diagnosis of acute cholecystitis. J. Nucl. Med. 14, 393 (1973) radioactivity accumulates in the gall bladder allowing visualization within 90 minutes of injection of $^{99m}$Tc-dihydrothioctic acid.

The objects of the present invention are to provide a more suitable diagnostic substance for gall bladder and biliary tract scanning.

SUMMARY OF THE INVENTION

This invention proposes the use of $^{99m}$Tc-pyridoxal or any amino acid derivative of pyridoxal labelled with technetium-99m or other radionuclide, including $^{99m}$Tc-pyridoxylidenemethioninate, $^{99m}$Tc-pyridoxylidenetyrosinate and in particular $^{99m}$Tc-pyridoxylideneglutamate. Compounds formed by the reaction of pyridoxal and amino acids labelled with $^{99m}$Tc, are included. The substances specified above all show sufficient accumulation in the gall bladder to enable this organ to be visualized by scintiscanning. In particular, $^{99m}$Tc-pyridoxylideneglutamate compares more than favourably with $^{99m}$Tc-D-penicillamine. In mice, the gall bladder is discernible by 8 minutes, and by 30 minutes scintiphotos of comparable quality to $^{99m}$Tc-D-penicillamine at 90 minutes were obtained. Similar results were obtained in dogs.

EXAMPLES

1. Preparation of $^{99m}$Tc-pyridoxylideneglutamate

Pyridoxal hydrochloride (54mg) and monosodium L-glutamate monohydrate (50mg) are dissolved in water for injection (2 ml) and $^{99m}$Tc-pertechnetate (20-25 mCi) is added. The pH is adjusted to 8–9 with 1 M sodium hydroxide and the mixture transferred to a rubber-closed vial. Air is displaced from the vial by passing nitrogen through the solution for 5 minutes, then the vial and contents are autoclaved at 120°C for one hour. After cooling, the preparation is ready for injection.

2. Preparation of $^{99m}$Tc-pyridoxylidenemethioninate

Pyridoxal hydrochloride (54mg) and DL-methionine (40mg) are reacted with $^{99m}$Tc-pertechnetate in a manner analogous to Example (1) above.

3. Preparation of $^{99m}$Tc-pyridoxylidenetyrosinate

Pyridoxal hydrochloride (54mg) and L-tyrosine (48mg) are reacted with $^{99m}$Tc-pertechnetate in a manner analogous to Example (1) above.

TOXICITY STUDIES

Pyridoxylideneglutamate was found to be without toxic effect in mice in doses up to 1,200 mg/kg (5000 times the human dose). The preparation was found to be sterile, pyrogen-free and non-antigenic.

USE IN PATIENTS

More than seventy patients have been injected intravenously with $^{99m}$Tc-pyridoxylideneglutamate (5–6 mCi) without adverse effects being noted. Following injection, the liver and biliary system are monitored using the gamma camera. Digital data are also stored on magnetic tape and allow computer processing to provide graphs showing activity variations with time in selected areas of the scan (heart, liver, gall bladder and intestine).

In normal humans, a hepatic parenchymal phase is observed within the first 5 minutes after injection. Radioactivity can then be seen collecting in the intrahepatic bile ducts and by 10 minutes begins to accumulate in the common bile duct and gall bladder. By 15–20 minutes, radioactivity enters the duodenum and uptake in the gall bladder continues to intensify.

In patients, the main use of this test is to discriminate between jaundice due to extrahepatic biliary obstruction or to hepatocellular disease. In the former case, radioactivity does not reach the colon as can be ascertained by examination of the patient scintigraphically fifteen hours after commencement of the study. In hepatocellular disease, however, 15 hour scintiphotos of the abdomen invariably show radioactivity in the bowel. In addition, the test will provide information concerning the anatomy and function of the gall bladder and biliary ducts. Although complimentary to radiological examination, this procedure may be of use when contrast media are contraindicated due to sensitivity reactions or other side effects, or when contrast studies are technically unsuccessful.

Preparation of $^{99m}$Tc-pyridoxylideneglutamate can be from a pre-mixed kit of the reagents, and an example of this is given.

PREPARATION OF THE KIT (5 vials)

Pyridoxal hydrochloride (270mg) and monosodium-L-glutamate monohydrate (250mg) are dissolved in pyrogen-free water (5 ml) and the pH adjusted to 9.0 using 1 M sodium hydroxide. The volume is adjusted to 10.0 ml with pyrogen-free water and the solution sterilized by membrane filtration. 2.0 ml aliquots are dispensed into each of 5 × 5 ml sterile rubber-closed vials and the air is displaced by passing sterile nitrogen through each vial for 5 minutes. Solutions prepared in this way appear to be biologically effective for at least 6 weeks.

LABELLING THE REAGENT $^{99m}$Tc-pertechnetate solution (20–25 mCi) are added to one vial and autoclaved for 1 hour. After cooling, the contents are ready for injection.

QUANTITY OF REAGENTS

1. The quantities of reagents specified here may of course be varied for the preparation of any given number of vials.

A similar kit may be formed containing the reagents in the solid state. This may be achieved by freeze-drying (or lyophilization) of a sterile solution, or by other means.

We claim:

1. A radiopharmaceutical for cholescintigraphy formed by the reaction of pyridoxal and amino acids labelled with a radionuclide.

2. A pharmaceutical according to claim 1 wherein said amino acid is glutamic acid.

3. A radiopharmaceutical according to claim 1 prepared by reacting the pyridoxal and an amino acid and radionuclide in pyrogen-free water, then adjusting the pH to 8–9 and displacing air therefrom with nitrogen and autoclaving and cooling whereby to produce a sterile, pyrogen-free non-antigenic solution for injection.

4. A pharmaceutical according to claim 1 wherein the radionuclide is technetium-99m.

5. A radiopharmaceutical according to claim 1 prepared by dissolving pyridoxal hydrochloride and monosodium L-glutamate monohydrate in pyrogen-free water with the addition of $^{99m}$Tc-pertechnetate, adjusting the pH to 8–9, transferring the mixture to a closed vial and displacing the air with nitrogen, autoclaving the contents of the vial, and cooling, whereby to obtain a sterile, pyrogen-free non-antigenic solution for injection.

6. A radiopharmaceutical according to claim 5 wherein the proportions used are approximately 50mg pyridoxal hydrochloride, 50mg monosodium L-glutamate monohydrate, dissolved in 2ml pyrogen-free water, 20–25 mCi $^{99m}$Tc-pertechnetate, and the reaction product is autoclaved at about 120°C for 1 hour.

7. A pharmaceutical according to claim 5 wherein the pH is adjusted by adding sodium hydroxide.

8. A pharmaceutical wherein the product of claim 1 is freeze-dried and subsequently labeled with the radionuclide.

9. A process for cholescinigraphy comprising intravenously introducing the product of claim 1 into a patient's system and monitoring the system by scintiscanning.

* * * * *